US005625664A

United States Patent [19]
Berkley

[11] Patent Number: 5,625,664
[45] Date of Patent: *Apr. 29, 1997

[54] METHODS FOR THE DESIGN, QUALITY CONTROL, AND MANAGEMENT OF FATIGUE-LIMITED METAL COMPONENTS

[75] Inventor: Stanley G. Berkley, Jupiter, Fla.

[73] Assignee: Fatigue Management Associates LLC, Palos Verdes, Calif.

[ * ] Notice: The term of this patent shall not extend beyond the expiration date of Pat. No. 5,490,195.

[21] Appl. No.: 540,876

[22] Filed: Oct. 11, 1995

Related U.S. Application Data

[63] Continuation-in-part of Ser. No. 245,011, May 18, 1994, Pat. No. 5,490,195.
[51] Int. Cl.$^6$ .................................................. G01N 23/20
[52] U.S. Cl. .............................................................. 378/72
[58] Field of Search ................................ 378/58, 59, 70, 378/72, 71

[56] References Cited

U.S. PATENT DOCUMENTS

| | | | |
|---|---|---|---|
| 3,762,885 | 10/1973 | Speirs et al. | 29/196.2 |
| 4,034,585 | 7/1977 | Straub | 72/53 |
| 4,095,103 | 6/1978 | Cohen et al. | 250/277 |
| 4,191,599 | 3/1980 | Stickels et al. | 148/16.5 |
| 4,561,062 | 12/1985 | Mitchell | 364/555 |
| 4,686,503 | 8/1987 | Ruud | 364/508 |
| 5,125,016 | 6/1992 | Korhonen et al. | 378/72 |
| 5,490,195 | 2/1996 | Berkley | 378/72 |

OTHER PUBLICATIONS

Yang, "Application of QNDE to Retirement–For–Cause Analysis, School of Engineering and Applied Science", pp. 101–119.

Forney, Jr., "Evolving Partnership for NDE in Materials Engineering and Extended Life Cycle Performance", *Review of Progress in QuantitativeNondestructive Evaluation*, vol. 10A, pp. 13–33.

Suresh, S., "Some Design Considerations and Case Studies," *Fatique of Metals*, Cambridge University Press, New York, 1991, pp. 499–502.

Flyer for "AST S2001, X–Ray Stress Analyzer," American Stress Technologies, Inc., Pittsburgh, PA.

Flyer for "AST S2002, X–Ray Stress Analyzer," American Stree Technologies, Inc., Pittsburgh, PA.

Flyer for "The TEC 1600 Series Stress Analysis System", The TEC Stress Analysis Group, Knoxville, TN.

Kirk, D., "Residual Stresses and Retained Austeinite in Shot Peened Steels", First International Conference on Shot Peening, Paris 14–17 Sep. 1981, pp. 271–277.

Coulon, A., "Effect Of The Honing Drum Upon The Inducement Of Compressive Residual Stresses," *Journal of Mechanical Working Technology*, 8 (1983) pp. 161–169.

Harting, M., and G. Fritsch, "A Non–destructive Method to Determine the Depth–Dependence of Three–dimensional Residual Stress States by X–ray Diffraction," *J. Phys. D: Appl. Phys.*, 26 (1993) pp. 1814–1816.

Kuhn, H. A., "An X–Ray Study of Creep–Deformation Induced Changes of the Lattice Mismatch in the gamma- –Hardened Monocrystalline Nickel–Base Superalloy SRR 99", *Asta Metall. Mater.*, vol. 39, No. 11, pp. 2783–2794, 1991.

Mequid, S. A., *Impact Surface Treatment*, International Conference on Impact Treatment Processes (2d:1986: Cranfield Institute of Technology).

Daly, J. J., "Status of Controlled Shot–Peening Technology in the United States", Metal Improvement Company, Paramus, New Jersey, pp. 237–241.

Taira, S. et al., "Local Residual Stress Near Fatigue Crack Tip", *Transactions ISU*, vol. 19, 1979, pp. 411–418. Parly published in *Journal of The Society of Materials Science, Japan*, 27 (1978), 251, in Japanese. English Version Jul. 18, 1978.

Delitizia, A. T., "Improving Fatigue Life Through Advanced Shot Peening Techniques", *Manufacturing Engineering*, May 1984, pp. 85–87.

*Primary Examiner*—Don Wong
*Attorney, Agent, or Firm*—Fitch, Even, Tabin & Flannery

[57] ABSTRACT

Improved methods for managing a population of metal components subject to fatigue failure are provided. The residual compressive stress in the critical surfaces of such components, especially in areas of high stress concentration, are measured non-destructively using x-ray diffraction techniques. The measured surface residual compressive stress is used as a management criterion. A component having a surface residual compressive stress greater than a predetermined value can be returned to service. However, once the measured surface residual compressive stress of a component falls below the predetermined value, it can either be removed permanently from service, or it can be reworked to increase its surface residual compressive stress and then returned to service. Additionally, by measuring the surface residual compressive stress of an individual component, the remaining service life of that individual component can be estimated. These methods for management of populations of such metal components allow for increasing the service life of the components in a safe and effective manner. Methods are also provided for the manufacture and/or design of metal parts with improved performance criterion (e.g., reduction in weight) while maintaining acceptable service life. Methods are also provided for establishing quality control procedures using surface residual compressive stress measurements during and/or after the manufacturing process in order to prevent, for example, introduction of metal parts having insufficient surface residual compressive stress levels for their intended use.

27 Claims, 1 Drawing Sheet

METHODS FOR THE DESIGN, QUALITY CONTROL, AND MANAGEMENT OF FATIGUE-LIMITED METAL COMPONENTS

RELATED APPLICATION

This is a continuation-in-part application of U.S. patent application Ser. No. 08/245,011, filed May 18, 1994, now U.S. Pat. No. 5,490,195 entitled "Method for Measuring and Extending the Service Life of Fatigue-Limited Metal Components," which is hereby incorporated by reference.

FIELD OF THE INVENTION

This invention generally relates to methods for managing the service life of fatigue-limited metal components. This invention also generally relates to a method for managing and extending the service life of fatigue-limited metal components. More specifically, this invention is related to a management method using a non-destructive technique for measuring the remaining useful service life of fatigue-limited metal components by determining the residual compressive stress in the critical surfaces of the individual components. Using the method of this invention, a metal component is removed from service or reworked to increase its residual compressive stress once the residual compressive stress is reduced or falls below a predetermined value. This invention allows an increase in both safety and economy in the management and operation of turbine engines and other machines containing fatigue-limited metal components by providing a reliable means for non-destructively measuring the remaining service life of the fatigue-limited metal components. This invention is especially adapted for managing populations of fatigue-limited rotating parts in gas turbine engines, including aircraft engines, and the like. Using the present methods of this invention to manage and measure the surface residual compressive stress in such parts or components, it is now possible to determine the appropriate time (i.e., prior to permanent deterioration from tensile stress crack initiation) for reworking the part to increase or restore its surface residual compressive stress so that the service life of the part or component can be extended. Using the present methods of this invention, the overall service life of a population of components used in, for example, jet engines or turbine engines, can be maximized without a significant decrease in safety. In fact, the present invention can provide both increased safety and economy for the aviation and other industries.

In another embodiment, this invention also generally relates to a method for designing fatigues limited metal components with selected service life and performance (e.g., weight) characteristics. More specifically, this embodiment provides a method in which the surface residual compressive stress measurements of a component during manufacture and/or design are used to guide manufacture and/or design so that the component can be manufactured and/or designed to have suitable and predictable service life while adjusting a performance criterion (e.g., reducing the weight) or several performance criteria of the component. In effect, a selected performance criterion (or several selected performance criteria) and service life of the component can be balanced to achieve optimum or near optimum performance/service life characteristics for specific components. Using weight reduction as the primary performance criterion, for example, such a method should be especially useful in military fighter aircraft where weight concerns are especially important, more limited component service lives are acceptable, and more frequent inspections are justified. Surface residual compressive stress measurements after one or more appropriate manufacturing step in the manufacturing process can also be used for quality control purposes.

BACKGROUND OF THE INVENTION

Fatigue-limited metal components of gas turbines or jet engines, or other machine components subject to metal failure or fatigue, must be carefully managed in order to avoid failure during operation. The failure, for example, of a critical component of a jet engine during operation may result in loss of life or other catastrophic consequences. Currently in the aviation industry (commercial and military), there are three general types of management techniques or approaches used for the management of fatigue-limited machine components in order to prevent possible catastrophic failure due to metal fatigue. Each of these approaches attempts to balance safety and economic concerns based on available data. See, for example, S. Suresh, *Fatique of Metals*, 499–502 (1991), which generally discusses the three commonly used management approaches.

The most conservative of these approaches, often termed the "safe life" approach, is based on the estimated fatigue life established through analysis and comparable experience by the engine manufacturer. This approach attempts to estimate the point at which the shortest-lived part or component in the total population would be expected to fail. After allowing for a suitable safety margin, an arbitrary retirement point is adopted for that component. This retirement point is normally measured in total take-off cycles or hours. Once a part reaches the retirement point, it is removed from service and mutilated to prevent further, unauthorized use. Although generally allowing for the greatest margin of safety, significant economically useful service life of such parts is lost. In effect, this "safe life" approach is based on, and controlled by, an estimation of the lifetime of the weakest part or component in the total population.

A somewhat less conservative management technique is the so-called "fail safe" approach. In this approach, a maximum service life is determined by the total accumulated service hours or cycles (whichever is shorter) at which the first crack is detected in an actual part (e.g., disk or drum rotor used in a compressor, turbine, or engine) in the population of like parts. Once a part has developed such a crack, its accumulated service life (in hours or cycles) is effectively used to determine the allowable service life of all similar parts in the population. If a part is later found to develop a crack at an earlier time then that part is used to redefine (and shorten) the acceptable service life limits of the population. Once a part reaches its acceptable service life, it is removed from service and mutilated to prevent further use. In effect, this "fail safe" approach is also based on, and controlled by, the actual weakest part or component in the total population. Many parts may still have many hours of safe and useful service life remaining beyond that of this weakest part. But, since the useful and safe service life of these parts cannot be reliably determined, they must be removed from service in the interest of safety. This "fail safe" approach is generally used in the airline industry for mature fleets where low cycle fatigue cracks have been detected in the relevant component populations. Where sufficient service data have not been developed, the more conservative "safe life" approach is generally used. In each approach, however, parts having many remaining hours of safe and reliable use will be removed from service.

More recently, the United States Air Force has successfully adopted an even less conservative management technique, the so-called "retirement for cause" approach, for its management of some critical engine components. In this approach, the parts are periodically examined non-destructively for cracks and other defects using, for example, fluorescent dye penetration, magnaflux, radiographic, or eddy current techniques. Once a crack is observed, that part, but only that part, is immediately retired from service. Other parts, even though they may have accumulated service times equal to or greater than the retired part, are continued to be used until they actually develop cracks. To operate safely, this approach requires frequent and periodic inspections of the individual parts. In general, as parts age, the frequency of inspections should be increased. In any event, the frequency of inspections must be such that the period between inspections is less, preferably by a significant margin, than the time normally required for a detectable crack to further deteriorate to the point of actual failure. Although this approach may result in more frequent teardowns for inspection of the individual parts, the potential savings based on achieving, or at least approaching, the maximum lifetimes of the individual parts can be enormous. The major drawback of this approach is that it relies upon detection of an actual crack in the part. Thus, this approach is generally not suitable for parts in which crack formation cannot be detected in a reliable and consistent manner. Once a crack has formed, the part contains, in effect, a permanent, irreversible defect which will ultimately lead to failure, perhaps catastrophic failure, unless that part is removed from service in a timely manner. Additionally, this approach, of course, is not suitable for use where the normal time between the initial development of a detectable crack and failure of the part is relatively short. Moreover, in parts where actual failure normally does not follow quickly after the development of a crack, if such a crack develops shortly after an inspection, the risk of failure during actual operation increases simply because the length of time in which the part is operated with the defect is maximized. Therefore, this method has an increased safety risk when compared to the "safe life" and "fail safe" approaches. This increased risk, although perhaps small, may still be significant because the detection point is the actual formation of a detectable crack. The longer that part remains in service, once a crack has formed, the greater the risk of catastrophic failure.

It would be desirable, therefore, to provide non-destructive methods to measure the remaining service or useful life of fatigue-limited metal components before crack initiation has begun or, at least, before actual cracks can be observed (i.e., before permanent and irreversible damage has begun). It would also be desirable to provide methods by which the service or useful life of fatigue-limited metal components could be increased without significantly increasing the risk of catastrophic failure of the metal components during operation. It would also be desirable to provide a method for manufacture and/or design of fatigue-limited metal components whereby the service life and selected performance criterion (e.g., weight) of the metal components can be adjusted and balanced to desired inter-related levels. It would also be desirable to provide a non-destructive method for determining the suitability of newly manufactured or reworked parts for their intended use. It would also be desirable to provide improved quality control methods or procedures for use in the manufacture of fatigue-limited metal components. Such methods would provide both increased safety and economy for the aviation industry (commercial and military). The methods of this invention generally provide such improved methods.

SUMMARY OF THE INVENTION

The present invention relates to methods for the management of populations of fatigue-limited metal components. This invention also relates to methods for the determination of the remaining service life of individual fatigue-limited metal components. The metal components to be managed by the present invention include metal components having relatively high levels of residual compressive stress as manufactured and which are subject to fatigue-related failure. The relatively high residual compressive stress of such a metal component as manufactured may be the result of the actual manufacturing process used and/or subsequent working of the metal component by shot peening or other cold working processes after actual production to increase the residual compressive stress. Preferably, the residual compressive stress as manufactured is in the range of about 50,000 to 200,000 pounds per square inch and, more preferably, in the range of about 150,000 to 180,000 pounds per square inch. Components having residual compressive stresses higher or lower than these ranges can, of course, be managed by the methods of the present invention. However, the components as manufactured should have sufficient residual compressive stress for their intended use. Using the methods of this invention, increases in both safety and economy in the management of such metal components are expected.

In another embodiment, this invention also relates to methods for the manufacture and/or design of fatigue-limited metal components whereby the surface residual compressive stresses are monitored and adjusted during manufacture and/or design to yield components having improved performance criterion (e.g., reduced weight) but still acceptable surface residual compressive stresses and, thus, acceptable service lifetimes. These methods can also be used during the manufacturing process to track and assess individual process steps by measuring the surface residual compressive stress and comparing it to design or target levels throughout the process. These values can also, if desired, be included in total stress calculations and/or a database for the components to assist in improving, evaluating, and/or understanding component design and performance. Components manufactured and/or designed using this method can then be, if desired, managed in service using the other methods disclosed and described herein for the management of populations of fatigue-limited metal components.

In still another embodiment, this invention also relates to quality control methods whereby the residual compressive stress condition of one or more critical surfaces areas is determined prior to entry of that part into service or at various stages during the manufacturing process. Parts having insufficient surface residual compressive stress levels for their intended purpose could either be withheld from service (and destroyed) or, if appropriate, reworked to increase the surface residual compressive stress of the part to acceptable levels. By avoiding placing parts into service with less than acceptable surface residual compressive stress levels and/or reducing the scatter or range of the residual compressive stress levels of parts placed into service, increased safety margins and economies can be obtained. Such quality control methods can also be used during the manufacturing process by measuring the residual compressive stress condition of one or more critical surfaces areas at various stages of the manufacturing process and using that measurement to determine whether that component (perhaps with reworking at that or later stages) can be continued in the manufacturing process. By early elimination of components not likely to pass final inspection or quality control requirements, considerable saving could be maintained. Moreover, increased quality control measures at various manufacturing stages will likely result in increased safety margins since potentially defective parts are more likely to be identified before entry into service. Such quality control methods can be used, if desired, on only one or only a few manufacturing steps in the process (e.g., control and evaluation of the shot peening process only).

Fatigue failures in metal components almost always develop from cracks generated in the surface layer of the metal components exposed to high stress environments. To reduce the likelihood of crack formation, great care is normally taken in the manufacture of such metal components to ensure that the initial residual stress in the critical surface layers of the crystalline structure of the metal are in relatively high compression (often up to 170,000 pounds per square inch or higher). Since these initial stress levels are not currently measured for the as-manufactured parts, it is possible that parts having less than acceptable residual compressive stress levels could be placed into service. During operation under conditions of high load and operating temperatures, the residual compressive stress of the component gradually diminishes over time. Once the residual compressive stress reaches zero, the trend continues and builds up residual tensile stress in these areas. Over time, the residual tensile stress can increase to levels in excess of the ultimate tensile strength of the surface of the material and cracks develop. Such cracks in a component left in service propagate until they reach a critical length, at which time catastrophic failure occurs. If such a part is placed into service with less than acceptable surface residual compressive stress values, catastrophic failure may occur (or at least be at increased risk to occur) before the first scheduled inspection. The present invention provides methods for managing metal components whereby conditions involving significant residual tensile stress and, therefore, crack initiation are avoided. By monitoring the residual compressive stress in areas of high stress concentration and maintaining the metal component under conditions of compressive stress, the present invention provides a management program which does not rely on either expected or actual crack formation as the management criterion. Further, the present invention provides a quality control method whereby the actual residual compressive stress levels in as-manufactured parts (and/or at critical stages of the manufacturing process) are measured so that parts without sufficient surface residual compressive stress for their intended purposes are identified (and corrected) before being placed into service.

In the method of this invention, a non-destructive technique (i.e., x-ray diffraction) is used to measure the remaining residual compressive stress in the relevant metal components. Once the residual compressive stress of an individual component falls below a predetermined value, that part, but only that part, is effectively flagged for further attention. For metal components having residual compressive stress below a predetermined value, there are essentially two options. In the first option, the metal component is simply removed permanently from service. In the second option, the metal component is reworked (using, for example, shot peening) to increase its residual compressive stress to an acceptable level and then returned to service. By periodically evaluating such metal components using the methods of this invention, the service life of the total population of metal components can be maximized in a safe and efficient manner.

For metal components having residual compressive stress higher than the predetermined value, the remaining service life of that component can be determined. The greater the difference between the measured residual compressive stress and the predetermined value, the greater the remaining service life for that component should be. Such information should be useful (especially as considerable historical data for the population become available over time) in matching components for use in particular engines or applications (i.e., matching components which have comparable remaining service life) or for scheduling routine teardowns and maintenance.

In the method of the present invention directed to manufacture and/or design/development of fatigue-limited metal components, the surface residual compressive stress is monitored during the manufacture and/or design/development process and used as a guide to obtain metal components having, for example, reduced weight but acceptable strength and service lifetimes. By measuring the surface residual compressive stresses during various stages of the manufacturing and especially during the course of the design and/or development process, the minimum (or near minimum) weight necessary for a given part or area of a part can be achieved while still maintaining an acceptable residual compressive stress in the critical surface areas of the part. Thus, using this method it is possible to manufacture and/or design fatigue-limited metal components with reduced weights and acceptable service lifetimes and inspection/maintenance schedules. This method will be especially useful in manufacturing and/or designing metal components (e.g., jet engine disks) for military aircraft. In effect, the design process of this invention allows the total stress (applied plus residual stresses) of the component during use to be taken into account in the design and/or manufacture procedures. In prior art design processes, generally only the applied stress could be taken into account.

One object of the present invention is to provide a method for managing a population of metal parts in order to determine when to remove an individual metal part from service, wherein said metal parts are manufactured having relatively high levels of residual compressive stress and said metal parts are subject to fatigue-related failure, said method comprising:

(1) selecting an individual metal part from the population;

(2) determining the remaining residual compressive stress of the surface of the selected individual metal part in one or more areas of stress concentration using x-ray diffraction techniques; and (3) removing the selected individual metal part from service if the remaining residual compressive stress measured in one or more areas of stress concentration has fallen below a predetermined level.

Another object of the present invention is to provide a method for managing a population of metals parts in order to extend the service life of individual metal parts in the population, wherein said metal parts are manufactured having relatively high levels of residual compressive stress and said metal parts are subject to fatigue-related failure during service, said method comprising, for each individual metal part in the population:

(1) removing the individual metal part from the population from service;

(2) measuring the remaining residual compressive stress of the surface of the individual metal part in one or more areas of stress concentration using x-ray diffraction techniques;

(3) comparing the remaining residual compressive stress measured in one or more areas of stress concentration to a predetermined level; and (4) if the remaining residual compressive stress remains above the predetermined level, returning the individual metal part to service; or (5) if the remaining residual compressive stress is at or below the predetermined level, reworking the individual metal part to increase the residual compressive stress to a reworked level above the predetermined level and then returning the individual metal part to service.

Although the present invention is preferably directed towards methods for the management of large populations of similar type metal parts, it can also be used to test individual metal parts. Thus, for example, the present invention can also be used for spot checking metal parts throughout their expected service life as part of routine or scheduled preventive maintenance or during repairs or teardown procedures necessitated by breakdowns. Thus, still another object of the present invention is to provide a method for determining when to remove a metal part from service, wherein said metal part is manufactured having relatively high levels of residual compressive stress and said metal part is subject to fatigue-related failure, said method comprising:

(1) measuring the remaining residual compressive stress of the surface of the metal part in one or more areas of stress concentration using x-ray diffraction techniques;

(2) comparing the remaining residual compressive stress measured in one or more areas of high stress concentration to a predetermined value; and (3) removing the metal part from service if the remaining residual compressive stress measured in one or more areas of stress concentration is less than the predetermined level.

Still another object of the present invention is to provide a method for extending the service life of a metal part, wherein said metal part is manufactured having relatively high levels of residual compressive stress and said metal part is subject to fatigue-related failure during service, said method comprising:

(1) measuring the remaining residual compressive stress of the surface of the metal part in one or more areas of stress concentration using x-ray diffraction techniques;

(2) comparing the remaining residual compressive stress measured in one or more areas of stress concentration to a predetermined level; and (3) if the remaining residual compressive stress remains above the predetermined level, returning the metal part to service; or (4) if the remaining residual compressive stress is at or below the predetermined level, reworking the metal part to increase the residual compressive stress to a reworked level above the predetermined level and then returning the metal part to service.

Still another object of the present invention is to provide a method for designing a fatigue-limited metal part whereby a selected performance criterion for the metal part is improved while maintaining sufficient residual compressive stress to achieve an acceptable service life for the metal part, said method comprising:

(1) providing a prototype of the metal part;

(2) measuring the residual compressive stress in one or more critical surface areas of the prototype during the course of design of the metal part;

(3) modifying the prototype using the difference between the measured residual compressive stress and a predetermined residual compressive stress design level as a guide to improve the selected performance criterion;

(4) remeasuring the residual compressive stress in the one or more critical surface areas of the modified ms prototype to determine the remeasured residual compressive stress in comparison to the predetermined residual compressive stress design level in order to gauge the effect of the modification; and (5) repeating steps (2) through (4) for the one or more critical surface areas until an acceptable and functional metal part is obtained, wherein the acceptable and functional metal part has its selected performance criterion improved and has sufficient residual compressive stress in the one or more critical surface areas for its intended use.

Still another object of the present invention is to provide a method for designing a fatigue-limited metal part whereby the weight of the metal part is reduced while maintaining sufficient residual compressive stress to achieve an acceptable service life for the metal part, said method comprising:

(1) providing a prototype of the metal part;

(2) measuring the residual compressive stress in one or more critical surface areas of the prototype during the course of the design of the metal part;

(3) modifying the prototype using the difference between the measured residual compressive stress and a predetermined residual compressive stress design level as a guide;

(4) remeasuring the residual compressive stress in the one or more critical surface areas of the modified prototype to determine the remeasured residual compressive stress in comparison to the predetermined residual compressive stress design level in order to gauge the effect of the modification; and (5) repeating steps (2) through (4) for the one or more critical surface areas until an acceptable and functional metal part is obtained having reduced weight and sufficient residual. Compressing stress in the one or more critical surface areas for its intended use.

Still another object of the present invention is to provide a method for designing a fatigue-limited metal part whereby the weight of the metal part is minimized while maintaining sufficient residual compressive stress to achieve an acceptable service life and safety factor for the metal part, said method comprising:

(1) providing a prototype of the metal part;

(2) measuring the residual compressive stress in one or more critical surface areas of the prototype during the course of the design of the metal part;

(3) modifying the prototype by reducing its weight using the difference between the measured residual compressive stress and a predetermined residual compressive stress design level as a guide;

(4) remeasuring the residual compressive stress in the one or more critical surface areas of the modified prototype to determine the remeasured residual compressive stress in comparison to the predetermined residual compressive stress design level in order to gauge the effect of the modification; and (5) repeating steps (2) through (4) for the one or more critical surface areas until an acceptable and functional metal part is obtained having minimal weight and sufficient residual compressive stress in the one or more critical surface areas to achieve an acceptable service life and safety factor for the metal part.

Still another object of the present invention is to provide a quality control method for the manufacture of fatigue-limited metal components, said method comprising measuring the residual compressive stress in one or more critical surface areas for each metal component after its manufacture and before placing it into services comparing the measured residual compressive stress in one or more critical surface areas to a corresponding predetermined residual compressive stress level for the one or more critical surfaces, and flagging each metal component which has its measured residual compressive stress below its corresponding predetermined residual compressive stress level, whereby flagged metal components are not placed in service. For purposes of this inventions "after its manufacturing" is intended to include selected stages during the manufacturing process as well as after completion of the entire manufacturing process. Likewise, "placed into service" is intended to include continuing beyond a specific manufacturing stage where measurements are made during the manufacturing stage as well as actual placement in service after completion of the manufacturing process.

These and other objects and advantages of the present invention will be apparent from a consideration of the present specification and drawing.

DETAILED DESCRIPTION OF THE INVENTION

The invention generally relates to methods for managing the service life of fatigue-limited metal components and to methods for managing and extending the service life of fatigue-limited metal components. The methods of this invention employ a non-destructive ms technique for measuring the remaining useful service life of fatigue-limited metal components by determining the residual compressive stress in the critical surfaces of the individual component. The surface residual compressive stress can be correlated with the remaining service life of the individual component. If the surface residual compressive stress has not fallen below a predetermined value, the component can be returned to service. If the surface residual compressive stress reaches or falls below a predetermined value, the component can be permanently removed from service. Or, if desired and appropriate, the component can be reworked to increase the surface residual compressive stress to a level above the predetermined value, preferably a value approaching the compressive stress of the component as originally manufactured, and then returned to service.

Figure 1:
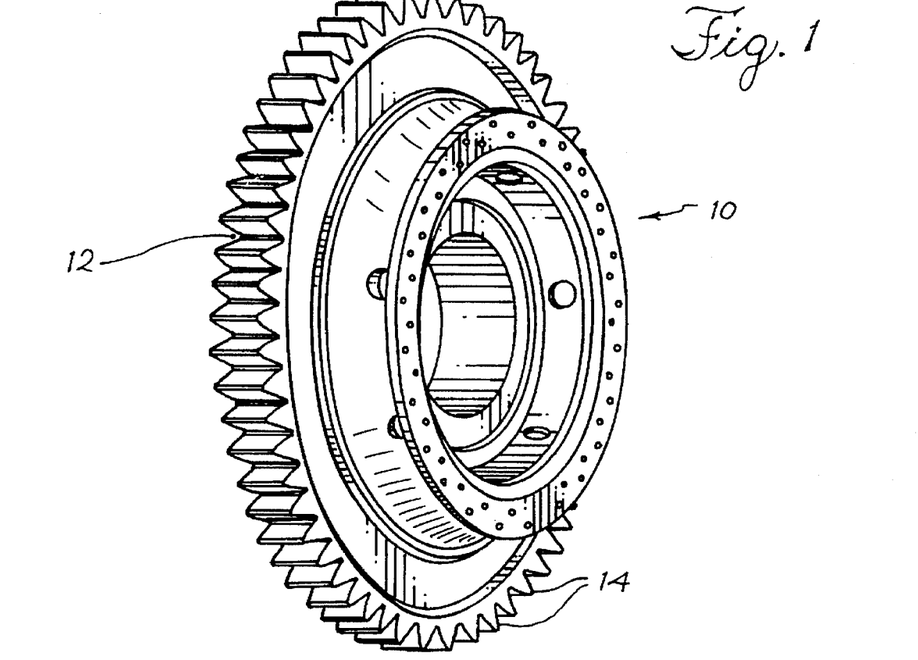
FIG. 1 illustrates a typical disk from a jet engine showing areas of stress concentration in which residual compressive stress should be determined.
Figure 2:
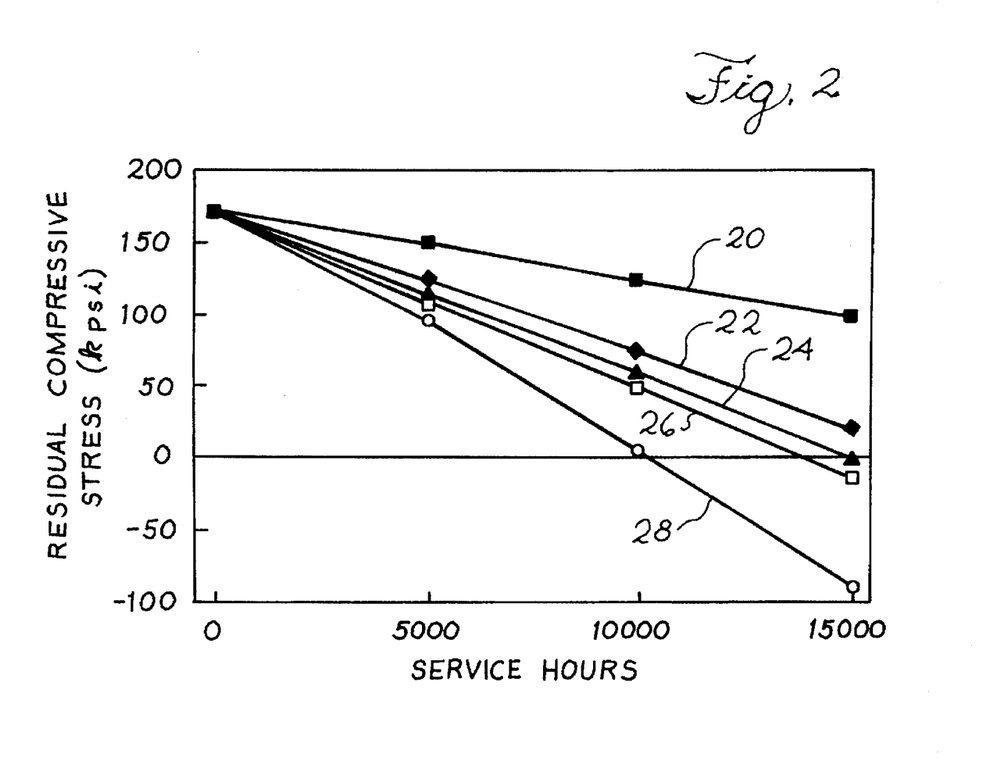
FIG. 2 shows a typical plot of residual compressive stress as a function of service time for turbine disks operating under different load and temperature conditions.

It is well established that fatigue failures develop from cracks generated in the surface layer of metal components exposed to high stress environments. For example, failure normally occurs because of cracks forming in areas of stress concentration in such components. FIG. 1 illustrates such a component, specifically a disk 10 for use in a gas turbine engine. Failure of such a disk is often caused by cracks forming in the surface layers of areas of high stress concentration such as the inside radii or bottom 12 of dovetail or firtree slots 14. These dovetail or firtree slots are used for attachment of the compressor and turbine blades (not shown). To reduce the likelihood of crack formation, great care is normally taken in the manufacture of such components to ensure that the initial residual stress in the critical surface layers of the crystalline structure of the metal are in high compression. (The actual value or level of the compression is not, however, determined in current manufacturing procedures.) For example, turbine disks, such as the one illustrated in FIG. 1, are generally manufactured with residual compressive stress in the order of about 170,000 pounds per square inch. During operation in a turbine engine (i.e., conditions of high load and operating temperatures), the residual compressive stress gradually diminishes over time as shown in FIG. 2. The curves in FIG. 2 (labeled 20, 22, 24, 26, and 28) are for different turbine disks 10 (i.e., different stages) used in a gas turbine engine. In such an engine, each disk is subjected to different load and temperature conditions during operation. Thus, the rate of decrease of the residual compressive stress is different for each disk or stage. Once the residual compressive stress reaches zero, residual tensile stress can build up in these areas. Over time, the residual tensile stress can increase to levels in excess of the ultimate strength of the surface of the material and cracks will initiate. Such cracks in a component left in service propagate until they reach a critical length, at which time catastrophic failure will occur. As seen in FIG. 2, the plot of residual compressive stress versus cycles is generally linear for a given component. Thus, residual compressive stress measurements of a given component which fall significantly off that part's linear curve may suggest a significant deviation or problem. For example, once a component departs significantly from the expected curve, the component may, for example, be moving from its elastic regime and into its plastic regime. Such deviations might also result from scatter in the original (i.e., as-manufactured) residual compressive stress conditions since components with significantly different initial residual compressive stress levels might have significantly different linear curves. Whatever the cause of the departure (even if the residual compressive stress value has not fallen below the predetermined value), the part should be examined more carefully and appropriate action taken (i.e., removed from service, reworked, or repaired as appropriate).

The methods of this invention monitor the residual compressive stress in surface areas of stress concentration in order to prevent the initial formation of cracks in the surface. By removing the component from service before the stresses change from compressive to tensile in nature or by maintaining the stress in compression, the present methods allow individual components to be used in a manner in which surface cracks are not formed or are, at least, formed at a significantly lower rate as compared to current management methods. The present methods allow for achievement of the maximum service life of components without increased failure or safety risks. Moreover, the present methods allow for significantly extending the service life of individual components without increased failure or safety risks.

In practice, for a given type and population of metal components, the residual compressive stress in the surface layer of the individual component is measured in one or more areas of stress concentration using x-ray diffraction techniques. The actual area measured is normally in the range of about ¼ by ¼ inches to about 1 by 1 inch, although smaller or larger areas can be used if desired. Generally it is preferred that the x-ray diffraction measurements be taken approximately normal to the relevant surface. Generally it is also preferred that the multiple x-ray measurements be taken within the relevant surface area so that the crystalline structure of that surface area can be better probed. The measured value (or values or averaged value) is compared to a predetermined value. If the measured value is above the predetermined value, the part can be returned to service. If however, the measured value equals or falls below this predetermined value, the component can be treated in several ways. In a first option, the component can be permanently removed from service. In such cases, it is generally preferred that the component be mutilated, or otherwise marked, to prevent further, unauthorized use. In a second option, the component can be reworked to increase its residual compressive stress and then returned to service. Normally, such a component can be reworked and returned to service a fixed number of times or cycles (i.e., until other failure mechanisms predominate or the component no longer meets design criterion or specifications). The acceptable number of cycles for reworking such components will generally be determined on a case-by-case basis. For a given component, such as the disk shown in FIG. 1, the cycle of service and reworking can generally be repeated so long as the component retains its dimensional and microstructural stability.

In some cases when the residual compressive stress is above, but close to or approaching, the predetermined value, it may be preferred to rework that part at that time rather than wait for the residual compression stress to fall below the predetermined value. For example, if the measured residual compressive stress suggests that the part has only a relatively short service life remaining before reworking will be required (see, for example, curve 22 in FIG. 2 at 15,000 hours with a predetermined value of zero pounds per square inch), it may be more economical to rework the part during the current scheduled shutdown/teardown event rather that put the part back in service and then require an unscheduled teardown to rework it only a short time later. Whether this modified approach is appropriate and desirable in a given case will depend, in larger part, on the expected service life before that part will fall below the predetermined value. If the expected remaining service life is short (thereby necessitating a unscheduled teardown for remeasurement), it may be more economical to rework that part even though it has remaining service life. In such a case, the predetermined value is effectively increased for that part only.

As one skilled in the art will realize, the predetermined value of the surface residual compressive stress for any given population of components will depend, at least in part, on the surface residual compressive stress of the components as originally manufactured, the specific physical and metallurgical characteristics of the components, the environment in which the components are used, and any appropriate safety factors. For populations of different parts, this predetermined value will likely be different because of different designs and/or geometries of the parts and exposure to different stresses during use. Populations of the same parts, but operated under different conditions and environments, may also have different predetermined values. Moreover, for a given component, different areas of stress concentration may have different predetermined values. For example, different areas of metal component will normally be exposed to, or will experience, different levels of stress and may, therefore, experience changes in the compressive stress at different rates. In such cases, the area that reaches its predetermined value first will normally control the disposition of that component. It will generally be preferred that the initial surface residual compressive stress of the metal components be measured or otherwise known before they are placed in service, or shortly thereafter. Measurement of the surface residual compressive stress of a component as originally manufactured can help insure that only components meeting specifications are used and can provide benchmarks for later measurements of remaining surface residual compressive stress. Moreover, such initial surface residual compressive stress data, along with the data generated by the present methods, can be used to define or redefine component specifications and design criterion as appropriate. Moreover, as detailed herein, such initial surface residual compressive stress measurements can form ah integral part of a comprehensive quality control program.

The predetermined value can be expressed in terms of absolute numbers (e.g., a specific value in suitable units for the residual compressive stress) or in relative numbers (e.g., a percentage of the remaining compressive stress of the component as compared to the residual compressive stress as originally manufactured). Moreover, the predetermined value for a given population may change over time as more historical data become available. For example, for newly designed components, it may be desirable to use a relatively high predetermined value to guard against unexpected failures for increased safety. As service life data become available, however, it may be appropriate to decrease the predetermined value if significant safety or failure related problems are not found in the population. By carefully adjusting the predetermined value for a given population of components over time, it should be possible to approach the optimum value while maintaining operational safety.

In some cases, a predetermined value of about zero pounds per square inch (or other appropriate units) or 100 percent decrease in residual compressive stress (i.e., the point at which stress moves from compressive to tensile in nature) may be appropriate. The use of zero pounds per square inch or 100 percent decrease as the management criterion might, for example, be appropriate to maximize the service life of a component where reworking the component is not practical or is otherwise not anticipated. In most cases, however, a predetermined value of a value greater than zero pounds per square inch or less than 100 percent decrease will generally be preferred and appropriate based on safety considerations. Such higher predetermined values will be especially preferred where reworking of the component to restore all or part of the residual compressive stress is anticipated. In some cases, however, a predetermined value of less than zero pounds per square inch or greater than 100 percent decrease may be appropriate.

As noted above, the residual compressive stress is measured non-destructively using conventional x-ray diffraction techniques. Preferably, the residual compressive stress is measured using portable x-ray diffraction equipment. Examples of such x-ray equipment and techniques can be found in U.S. Pat. No. 4,095,103 (Jun. 13, 1978); U.S. Pat. No. 4,561,062 (Dec. 24, 1985); U.S. Pat. No. 4,686,631 (Aug. 11, 1987); U.S. Pat. No. 5,125,016 (Jun. 12, 1992); Taira & Tanaka, "Residual Stress Near Fatigue Crack Tips," 19 *Transactions of the Iron & Steel Institute of Japan*, 411–18 (1979); Harting & Fritsch, "A Non-destructive Method to Determine the Depth-dependence of Three-dimensional Residual Stress States by X-ray Diffraction," 26 *J. Phys. D: Appl. Phys.*, 1814–16 (1993); Kuhn et al., "An X-ray Study of Creep-deformation Induced Changes of the Lattice Mismatch in γ-Hardened Monocrystalline Nickel-Base Superalloy SRR 99," 39 *Acta Metall. Mater.*, 2783–94 (1991), all of which are hereby incorporated by reference. Portable x-ray equipment, which is generally preferred in the present invention, can be obtained commercially from, for example, Technology for Energy Corporation (P.O. Box 22996, Lexington Drive, Knoxville, Tenn. 37933); or American Stress Technologies, Inc. (61 McMurray Road, Pittsburgh, Penn. 15241); or Proto Manufacturing Limited (2175 Solar Crescent, Oldcastle, Ontario, Canada N0R 1L0). Other types and designs of x-ray diffraction equipment or techniques can also be used in the present invention.

Normally such measurements should be made, at a minimum, during scheduled teardowns and other maintenance events. In some cases, however, it may be desirable to make such measurements more often than regularly scheduled maintenance events, especially during the early service life of a population of newly designed components lacking a extensive service life history. Normally, such measurements of the residual compressive stress will be made on the individual parts during teardowns. For some components, however, it may be possible to make the necessary measurements without having to perform complete teardowns. As noted above, x-ray diffraction measurements of residual compressive stress should be made in areas of high stress concentration (e.g., the bottom 12 of the firtree slots 14 on the disk 10 shown in FIG. 1). Generally, areas of high stress concentration are those areas in which crack formation has been observed or is more likely to occur. It is not necessary, however, to make such measurements in each and every area of high stress concentration in a given component, especially where such areas are operated under similar load and temperature conditions. For the disk in FIG. 1, for example, measurements might be taken on the bottom 12 of the firtree slots 14 located at 0, 90, 180, and 270 degrees, rather than at the bottom of every slot 14. The individual measurements at these representative locations, or an average of the individual measurements, are compared to the predetermined value. As the database develops, the number and location of measurements for a given disk (or other population of components) can be modified as appropriate.

Once a component reaches or falls below its predetermined value, it can either be removed permanently from service or reworked to increase its residual compressive stress to a level above the predetermined value and then returned to service. For example, using a predetermined value of zero pounds per square inch, the disk represented by curve 28 in FIG. 2 should be removed from service or reworked after about 10,000 hours of service; the disks represented by curves 24 and 26 should be removed from service or reworked after about 15,000 hours; the disks represented by curves 20 (especially) and 22 (to a lesser extent) have service lives greater than 15,000 hours. Preferably, the residual compressive stress in such reworked components is returned to a level approaching the original residual compressive stress as manufactured. Reworking such components can be carried out using conventional procedures for increasing or achieving residual compressive stress. Such methods include, for example, shot peening and other methods of cold working the surface (e.g., hammer peening, laser peening, rolling, or burnishing methods). See, for example, Daly, "Status of Controlled Shot-Peening Technology in the United States," International Conference on Impact Treatment Processes (2nd: 1986) in *Impact Surface Treatment* (Meguid, Ed.), 237–41; Delitizia, "Improving Fatigue Life Through Advanced Shot Peening Techniques," 92 Manufacturing Engineering, 85–87 (1984). Of course, such reworking must be carried out before any permanent deterioration occurs from residual stress cracking. Thus, where such reworking is anticipated, the predetermined value used as the management criterion preferably is higher (i.e., a higher predetermined value of residual compressive stress) than in cases where reworking is not anticipated. By setting the management criterion higher in such cases, one moves further away from the condition where crack formation, which may not even be detectable, may occur, thereby providing an increased margin of safety. It is generally preferred that reworking increases the residual compressive stress to at least 50 percent of the residual compressive stress in the part as originally manufactured. More preferably, the rework level for the residual compressive stress is at least 80 percent of the value as originally manufactured. Even more preferably, the reworked level is comparable to the value as originally manufactured.

The methods of this invention generally allow one to maximize the service life of a metal component by providing a procedure to determine when to optimally rework the metal component to restore all or part of the residual compressive stress. Excessive reworking can actually decrease the service life since reworking techniques such as shot peening can increase the dimension of the metal part in the reworked area. Thus, the likelihood of a metal component moving out of its design specification increases as a function of the number of times it is reworked. The present invention provides procedures whereby the maximum service life can be obtained with the minimum number of reworkings. Of course, the effect of reworking on dimensional stability should be taken into account when establishing the appropriate predetermined value for a given component.

The present methods for management of population of metal components provide considerable improvement over management methods currently in use. Both the "safe life" and "fail safe" methods rely on expected service life based on either predicted values or statistical values of crack formation in the weakest component in the population. In these methods, service life is not evaluated for individual components. Thus, the vast majority of components are retired while still possessing useful and significant service life. The "retirement for cause" approach relies on the observation of actual crack formation in a given component. Once crack formation is observed, that component is removed from service. Unfortunately, once crack formation can be observed, the component cannot be rehabilitated or reworked for additional service life. Additionally, at least in some cases, waiting for actual crack formation as a management criterion can result in significant safety risks. The methods of the present invention provide improved management procedures by providing management criteria (i.e., residual compressive stresses compared to predetermined values) which are observable well before irreversible crack initiation or formation occurs. Using the methods of the present invention, the maximum service life of such components can be obtained in a safe and effective manner. Using the methods of the present invention, at least some components can be reworked to increase the residual compressive stress and placed back in service, thereby providing increased efficiency without compromising safety. In fact, the methods of the present invention are expected to achieve improved efficiency and improved safety as compared to the management methods currently in use since the management criterion is based on surface residual compressive stresses rather than on actual or expected crack formation. By using surface residual compressive stress as the management criterion, rather than actual or expected crack formation, the margin of safety is expected to be increased, perhaps significantly.

The methods of the present invention are ideally suited for augmenting computer tracking of metal components during their service life. Moreover, the data generated from the present methods (i.e., residual compressive stress) and data regarding the service life and history of individual components can be used to develop a management database for the metal components. As the historical basis of such a database grows, it will be possible to reliably predict the service life of a given part. Thus, once such a database is developed, one will not need to measure the compressive stress of each and every component during each teardown or other maintenance event. If the total service life or history of the component is sufficiently short (as determined from the historical data in the database), measurement of the compressive stress can be delayed. Only such components having a service life or history approaching some definable parameter (again as determined from the historical data in the database) will be required to have the actual compressive stress measured and compared to the predetermined value. For example, for a given component, the database might show that only components having a service live in excess of 10,000 hours ever have residual compressive stresses approaching or below the predetermined value. In such a case, only components with service lives greater than this value will need to have the residual compressive stress measured during a routine teardown. Of course, components with abnormalities or components subjected to extreme service events should be evaluated regardless of the cumulated service life. Moreover, it may still be prudent to at least perform some spot checks on components with shorter service lives in order to confirm the continuing validity of the database and its predictive ability. By avoiding actual measurements for components very unlikely to have residual compressive stress values lower than the predetermined value, considerable savings can be obtained. Of course, the method used to predict this likelihood must be proven over time to be both effective and safe.

The present methods are not, however, intended to replace all non-destructive testing of such metal components. As those skilled in the art will realize, the present methods are designed to manage failures and defects related to crack initiation mechanisms commonly associated with the residual compressive stress and residual tensile stress levels in the surface layers. Other non-destructive testing methods for identifying other types of failures and/or failure mechanisms, especially early in the service life of such components (i.e., during the so-called "infant mortality" period), should be continued as appropriate. Incorporation of such data from other non-destructive testing procedures in the management database discussed above may allow even more complete tracking and management of populations of such metal components.

Additionally, using the methods of this invention, components of approximately equal remaining service life (i.e., approximately equal residual compressive stress) can be used together. Normally, the frequency of such teardowns in individual engines will be controlled by the component having the shortest remaining service life. By avoiding use of components of widely varying remaining service life, early teardown of engines, necessitated by a single component with only a short remaining service life, can be avoided. By matching components with similar remaining service lives in a given engine, the frequency of teardowns over the entire population can be reduced.

In another embodiment of this invention, the general techniques discussed above for measuring surface residual compressive stress can also be used to assist and guide the design and development of improved fatigue-limited metal components. Using this method, the surface residual compressive stresses produced by the various steps in the manufacturing process can be incorporated into, and taken into account in, the overall stress analysis. Effects of modification of the part design (e.g., reduction in weight) throughout the manufacturing and/or design/development process can be determined and used as a guide for further modifications. Using such an iterative approach, reduced-weight fatigue-limited metal parts can be designed having sufficient residual compressive stresses (i.e., sufficient service lifetimes) for their intended use. Thus, the component design can be fine tuned to reduce component weight without significant reduction (or at least reduction to known and acceptable levels) in service lifetimes. The service lifetime and weight characteristics can be balanced to achieve optimum or near optimum performance criterion. For military aircraft, such optimum or near optimum performance criterion may, for example, be related to a reduction in weight to improved thrust to weight ratios. For commercial aircraft, such optimum or near optimum performance criteria may, for example, be related to improved safety margins and/or increased engine performance. Of course, if desired, other appropriate performance criteria may be used to assist in designing fatigue-limited metal components using the methods of this invention.

Historically the design procedure for critical fatigue-limited metal components such as disks or other critical aircraft engine components has been the conservative "safe life" approach. This safe life design approach, like the corresponding safe life technique for managing a population of fatigue-limited parts, is generally based on manufacturer's estimated fatigue life established through analysis, testing, and comparable experience by the part manufacturer. This approach attempts to estimate the point, allowing for a suitable safety margin, at which the shortest lived part is expected to fail. The stress calculations used in this design approach are primarily based on applied stress.

The present method uses the measurement of the surface residual compressive stress during the manufacturing process as an important component of the design approach. The residual compressive stress is measured using x-ray diffraction periodically throughout the development and/or design process to assess the effects of various manufacturing operations or procedures used in making the component on the residual compressive stress in the critical surface areas of the component. The use of this method in the manufacture and/or design of new fatigue-limited parts will allow quantification of the surface residual compressive stress condition at each step in the manufacturing process; in addition, it will be possible to determine the positive or negative impact on the surface residual compressive stress condition as a result of each operation and, if appropriate, adjust or modify the operation or operations so as to provide the desired level of surface residual compressive stress in the finished metal part. By measuring or remeasuring the surface residual compressive stress after various machining operations, the design or development of the part may by guided whereby a preselected design or performance criterion (or several criteria) can be improved, and perhaps optimized, while still maintaining an adequate service life. Thus, this method can be used to set residual compressive stress part requirements and fine-tune component design to provide an optimized or near optimized performance criterion and service life. For example, this method could be used to fine tune component design to reduce the weight of specific aircraft engine parts while maintaining significant (and known) service life. A reduction in weight would, for example, benefit thrust to weight ratio in military aircraft applications and increase commercial aircraft engine performance. Acceptable surface residual compressive stress levels determined during the design process can, if desired, be included in component specifications and/or drawings and can be used during actual manufacturing processes. Such designed components could be managed using the other embodiments of this invention as described above. Balancing of one or more preselected performance criteria and service life to improve overall performance will be possible using the method of this invention.

In operation, the manufacturing and/or design/development method of this invention is carried out by first measuring the residual compressive stress, preferably using x-ray diffraction techniques, in one or more critical areas of a prototype or partially designed metal part. The prototype is then modified (i.e., machined or worked) using the difference between measured residual compressive stress and the predetermined residual compressive stress design level as a guide to improve the a selected performance criterion. The predetermined design level may be the residual compressive stress desired in the final metal part or an intermediate level or intermediate levels based on the entire manufacturing process. After modifying the part, the residual compressive stress is remeasured and compared to the predetermined design level to gauge the effect of the modification. Of course, as one skilled in the art realizes, this comparison of the remeasured residual compressive stress could also, if desired, be made to the previously measured residual compressive stress with similar results. The comparison allows the effect of each manufacturing process or stage on the residual compressive stress history to be determined. This process is repeated for one or more critical surface areas until an acceptable and functional metal part is obtained which has its selected performance criterion (or performance criteria) improved and has sufficient residual compressive stress values (and, therefore, acceptable service life) for its intended use.

Service life can refer to a total service life over the entire life of the part or, in the case where the part is reworked, the individual lifetimes between reworkings or the sum of all individual lifetimes between reworkings. The level of acceptable service life will, of course, vary for different parts. For example, a part which can be reworked easily for a significant number of times can generally have its selected performance criterion improved by accepting more frequent teardowns and reworking. For a part which cannot be reworked or which cannot be reworked easily, it will generally be preferred that the service life (especially between reworkings) be kept relatively long. In any event, the improvement in the selected performance criterion and the length of service life (both total and/or between reworkings) can be balanced and adjusted to optimum or near optimum levels for that metal part and its intended use and/or service environment.

In still another embodiment of this invention, the general techniques discussed above for measuring surface residual compressive stress can also be used to provide a quality control program or mechanism for the manufacture of fatigue-limited metal components. Using this embodiment, the residual compressive stress in one or more critical surfaces areas is measured after the component has been manufactured but before it is placed in service. If the residual compressive stress in one or more critical areas is below a corresponding predetermined residual compressive stress value for the one or more critical areas, the component is flagged or otherwise marked for further attention. If the residual compressive stress levels for the component are within acceptable ranges (i.e., for each of the one or more critical surface areas, the measured residual compressive stress is equal to or greater than the corresponding predetermined residual compressive stress value), then the component can be placed into service (assuming, of course, it meets other appropriate quality control requirements). The present quality control method is generally not intended to replace all existing quality control requirements; rather, it preferably supplements and strengthens the existing quality control program for fatigue-limited components. As one of ordinary skill in the art will realize, the predetermined residual compressive values for each of the more than one critical surface areas may be the same or different for other surface areas, depending on the actual geometry of the component and the different service conditions the various surfaces will be exposed to during use.

Of course, as one skilled in the art will realize, the present quality control procedure can be used during the manufacturing process as well as for the completed component. In other words, the measured surface residual compressive stress measurements for the partially completed component during one or more stages of the manufacturing process can be used to gauge or test the process up to that point before moving on in the manufacturing process. It is especially preferred that this quality control procedure be used to measure and control the effect of working the component to increase or modify the surface residual compressive stress. Thus, this quality control process is especially useful and preferred for quality control of the shot peening (or other working or reworking technique) step in the manufacturing process.

Flagged components (i.e., components having lower than acceptable residual compressive stress levels) are not placed into service as manufactured (or, if during the manufacturing process, are not moved to the next step). Such flagged components can be, if appropriate, destroyed or otherwise mutilated to prevent unauthorized use (or continuation of the manufacturing process for that component). Or in appropriate cases, the flagged metal components are reworked to increase the residual compressive stress in the one or more critical surface areas to levels above the corresponding predetermined residual compressive stress.

Assuming such reworked metal components then meets the surface residual compressive stress and other requirements, the reworked metal components can be placed in service (or the manufacturing process continued with the partially completed and reworked components). Flagged metal components which are especially suitable for reworking include metal components which only fail to meet the surface residual compressive stress requirements (i.e., all other quality control requirements are within specification). Appropriate reworking and/or modification of the component can, of course, be used to bring other quality control requirements within specification. Preferably, after reworking, all quality control parameters, including surface residual compressive stress levels, are remeasured to insure that the part has obtained, or remains within, the relevant specifications. Preferably, specific surface residual compressive stress levels, ranges, or targets are included in the detailed component specification and also directly on the relevant drawings. Data from measured surface residual compressive stress values during the manufacturing process and during later management of the population of parts (identifiable to specific component serial numbers or other identifiers) could be especially useful in failure analysis and statistical analysis of component populations.

The decision to rework a particular component can be informed by a number of factors, including the amount the measured residual compressive stress levels fall below the acceptable values for the one or more critical surface areas and/or, if appropriate, the stage in the manufacturing process at which the residual compressive stress levels fall below the acceptable values for one or more critical surface areas. If the component is only slightly out of specification, it is more likely that reworking will be cost effective. For components which are far out of specification, it may be more cost effective to simply destroy the part (especially if the amount of reworking necessary to bring the part within the surface residual compressive stress requirements is such that other quality control requirements cannot be achieved or maintained). Where surface residual compressive stress is measured at different stages of the manufacturing process, there will likely be stages at which failure to meet the corresponding specification may be more critical or which it will be more difficult to obtain a satisfactory result with reworking. Determining whether reworking is feasible and/or appropriate will preferably be, at least initially, on a case by case basis. Once significant historical data have been generated, a more statistical determination or analysis can likely be used (both where measurement are taken during various stages of the manufacturing process and/or at the end of the manufacturing process).

The quality control method of this invention offers a number of significant advantages over currently conducted manufacturing procedures for fatigue-limited components. First of all, it involves the direct measurement and tracking of an important fatigue-failure related parameter—the surface residual compressive stress. Historically, quality control procedures have not included the measurement of compressive stresses; rather, they have relied upon other "predicative" parameters which may not have been as directly related to, or as predictive in regard to, fatigue failure as desirable. Moreover, such earlier quality control procedures were likely to result in components having considerable scatter or ranges for the surface residual compressive stress levels over the range of the population (even assuming all residual compressive stress levels were above acceptable limits); moreover, the actual surface residual compressive stress values for the components are generally not even known. By not knowing the initial surface residual compressive stress levels (i.e., relying only on other predictive parameters), the ultimate user might place components into use which would fail much sooner than predicted by the prevalent management procedures.

Also in the earlier quality control procedures, it was not possible to match components (i.e., components with similar predictive service lifetime) in order to minimize teardown schedules and expenses. Such problems can be avoided to a large extent using the methods of this invention. For example, parts having similar predicted service lifetimes can be matched in a given jet engine. Teardowns, inspections, and regularly scheduled maintenance procedures can be tailored for the composite predictive lifetimes. Thus, where components are matched with relatively short predictive lifetimes (but still of acceptable lengths), appropriate inspections can be scheduled at a shorter time interval as compared to matched parts having a longer predicted lifetime. In this manner, the overall cost, safety, and reliability can be better maximized. In addition, the use of surface residual compressive stresses as a quality control parameter is also expected to reduce the number of component failures during the so-called "infant mortality" period.

The management, design, and quality control methods of this invention can also be used in conjunction with other management, design, and quality control method and/or techniques normally used with fatigue-limited metal components. For example, the present design method can be used with conventional finite element analysis design techniques. Such finite element analysis is generally used to calculate or determine the perceived high stress areas of a given component. By including the residual compressive stress levels into total stress considerations, the present methods can be used, for example, to fine tune the results of the finite element analysis and make it a more realistic and useful tool. As those skilled in the art will realize, the present methods can be used in conjunction with other management, design, and quality control techniques to improve those techniques and, overall, provide even better safety and economy in the use of such fatigue-limited components.

That which is claimed is:

1. A method for designing a fatigue-limited metal part whereby a selected performance criterion for the metal part is improved while maintaining sufficient residual compressive stress to achieve an acceptable service life for the metal part, said method comprising:

(1) providing a prototype of the metal part;

(2) measuring the residual compressive stress in one or more critical surface areas of the prototype during the course of design of the metal part;

(3) modifying the prototype using the difference between the measured residual compressive stress and a predetermined residual compressive stress design level as a guide to improve the selected performance criterion;

(4) remeasuring the residual compressive stress in the one or more critical surface areas of the modified prototype to determine the remeasured residual compressive stress in comparison to the predetermined residual compressive stress design level in order to gauge the effect of the modification; and (5) repeating steps (2) through (4) for the one or more critical surface areas until an acceptable and functional metal part is obtained, wherein the acceptable and functional metal part has its selected performance criterion improved and has sufficient residual compressive stress in the one or more critical surface areas for its intended use.

2. A method as defined in claim 1, wherein the residual compressive stress and the remeasured residual compressive stress are measured using x-ray diffraction techniques.

3. A method as defined in claim 1, wherein the metal part is a rotating part used in a gas turbine or jet engine.

4. A method as defined in claim 2, wherein the metal part is a rotating part used in a gas turbine or jet engine.

5. A method as defined in claim 3, wherein the metal parts is a disk or a drum rotor.

6. A method as defined in claim 4, wherein the metal part is a disk or a drum rotor.

7. A method as defined in claim is wherein the selected performance criterion is a reduction in weight of the metal part.

8. A method as defined in claim 3, wherein the selected performance criterion is a reduction in weight of the metal part.

9. A method as defined in claim 4, wherein the selected performance criterion is a reduction in weight of the metal part.

10. A method for designing a fatigue-limited metal part whereby the weight of the metal part is reduced while maintaining sufficient residual compressive stress to achieve an acceptable service life for the metal part, said method comprising:

(1) providing a prototype of the metal part;

(2) measuring the residual compressive stress in one or more critical surface areas of the prototype during the course of the design of the metal part;

(3) modifying the prototype using the difference between the measured residual compressive stress and a predetermined residual compressive stress design level as a guide;

(4) remeasuring the residual compressive stress in the one or more critical surface areas of the modified prototype to determine the remeasured residual compressive stress in comparison to the predetermined residual compressive stress design level in order to gauge the effect of the modification; and (5) repeating steps (2) through (4) for the one or more critical surface areas until an acceptable and functional metal part is obtained having reduced weight and sufficient residual compressive stress in the one or more critical surface areas for its intended use.

11. A method as defined in claim 10, wherein the residual compressive stress and the remeasured residual compressive stress are measured using x-ray diffraction techniques.

12. A method as defined in claim 10, wherein the metal part is a rotating part used in a gas turbine or jet engine.

13. A method as defined in claim 11, wherein the metal part is a rotating part used in a gas turbine or jet engine.

14. A method as defined in claim 12, wherein the metal part is a disk or a drum rotor.

15. A method as defined in claim 13, wherein the metal part is a disk or a drum rotor.

16. A method for designing a fatigue-limited metal part whereby the weight of the metal part is minimized while maintaining sufficient residual compressive stress to achieve an acceptable service life and safety factor for the metal part, said method comprising:

(1) providing a prototype of the metal part;

(2) measuring the residual compressive stress in one or more critical surface areas of the prototype during the course of the design of the metal part;

(3) modifying the prototype by reducing its weight using the difference between the measured residual compressive stress and a predetermined residual compressive stress design level as a guide;

(4) remeasuring the residual compressive stress in the one or more critical surface areas of the modified prototype to determine the remeasured residual compressive stress in comparison to the predetermined residual compressive stress design level in order to gauge the effect of the modification; and (5) repeating steps (2) through (4) for the one or more critical surface areas until an acceptable and functional metal part is obtained having minimal weight and sufficient residual compressive stress in the one or more critical surface areas to achieve an acceptable service life and safety factor for the metal part.

17. A method as defined in claim 16, wherein the residual compressive stress and the remeasured residual compressive stress are measured using x-ray diffraction techniques.

18. A method as defined in claim 16, wherein the metal part is a rotating part used in a gas turbine or jet engine.

19. A method as defined in claim 17, wherein the metal part is a rotating part used in a gas turbine or jet engine.

20. A method as defined in claim 18, wherein the metal part is a disk or a drum rotor.

21. A method as defined in claim 19, wherein the metal part is a disk or a drum rotor.

22. A quality control method for the manufacture of fatigue-limited metal components, said method comprising measuring the residual compressive stress in one or more critical surface areas for each metal component after its manufacture and before placing it into service, comparing the measured residual compressive stress in one or more critical surface areas to a corresponding predetermined residual compressive stress level for the one or more critical surfaces, and flagging each metal component which has its measured residual compressive stress below its corresponding predetermined residual compressive stress level, whereby flagged metal components are not placed in service.

23. A quality control method as defined in claim 22, wherein the flagged metal components are destroyed or otherwise mutilated to prevent unauthorized use.

24. A quality control method as defined in claim 22, wherein the flagged metal components are reworked to increase the residual compressive stress in the one or more critical surface areas to levels above the corresponding predetermined residual compressive stress, whereby the reworked metal components can be placed in service.

25. A quality control method as defined in claim 22, wherein the residual compressive stress in one or more critical surface areas for each metal component is determined using x-ray diffraction techniques.

26. A quality control method as defined in claim 23, wherein the residual compressive stress in one or more critical surface areas for each metal component is determined using x-ray diffraction techniques.

27. A quality control method as defined in claim 24, wherein the residual compressive stress in one or more critical surface areas for each metal component is determined using x-ray diffraction techniques.

* * * * *

UNITED STATES PATENT AND TRADEMARK OFFICE
CERTIFICATE OF CORRECTION

PATENT NO. : 5,625,664
DATED : April 29, 1997
INVENTOR(S) : Stanley G. Berkley

It is certified that error appears in the above-indentified patent and that said Letters Patent is hereby corrected as shown below:

Claim 7, Column 20, Line 54, change "is" to -- 1, --

Signed and Sealed this

Twenty-ninth Day of July, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,625,664
DATED : April 29, 1997
INVENTOR(S) : Stanley G. Berkley

It is certified that error appears in the above-indentified patent and that said Letters Patent is hereby corrected as shown below:

Title Page, Column 1, under "Other Publications", fifth reference, the flyer should be listed as: --Flyer for "AST S2002, X-Ray Stress Analyzer," American Stress Technologies, Inc., Pittsburgh, PA.--

Column 1, line 49, change "fatigues limited" to --fatigue-limited--.

Column 2, line 19, change "Fatique" to --Fatigue--.

Column 2, line 49, change "limits" to --limit--.

Column 8, line 6, delete "ms".

Column 8, line 41, change "residual. Compressing" to --residual compressive--.

Column 9, line 43, delete "ms".

UNITED STATES PATENT AND TRADEMARK OFFICE
CERTIFICATE OF CORRECTION

PATENT NO. : 5,625,664
DATED : April 29, 1997
INVENTOR(S) : Stanley G. Berkley

It is certified that error appears in the above-indentified patent and that said Letters Patent is hereby corrected as shown below:

Column 12, line 12, change "ah" to --an--.

Column 16, line 18, change "improved" to --improve--.

Column 16, line 56, change "by" to --be--.

Signed and Sealed this

Twenty-third Day of September, 1997

Attest:

BRUCE LEHMAN

Attesting Officer

Commissioner of Patents and Trademarks